(12) United States Patent
Fiedler et al.

(10) Patent No.: US 7,238,835 B2
(45) Date of Patent: Jul. 3, 2007

(54) PROCESS FOR THE PREPARATION OF SUBSTITUTED 2-(PHENOXYMETHYL) BENZOIC ACIDS

(75) Inventors: Wolfgang Fiedler, Eppstein (DE); Bernd Neises, Offenburg (DE); Jochen Hachtel, Frankfurt (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 365 days.

(21) Appl. No.: 11/018,038

(22) Filed: Dec. 21, 2004

(65) Prior Publication Data

US 2005/0171205 A1 Aug. 4, 2005

Related U.S. Application Data

(60) Provisional application No. 60/587,798, filed on Jul. 14, 2004.

(30) Foreign Application Priority Data

Dec. 22, 2003 (DE) ................ 103 60 525

(51) Int. Cl.
*C07C 65/00* (2006.01)
(52) U.S. Cl. .............. 562/473; 562/471; 562/475
(58) Field of Classification Search .......... 562/475, 562/473, 471
See application file for complete search history.

(56) References Cited

U.S. PATENT DOCUMENTS

| 4,499,299 A * | 2/1985 | Bernstein et al. ........... 514/570 |
| 5,221,762 A | 6/1993 | Wingert et al. |
| 2003/0072842 A1 | 4/2003 | Johnson et al. |

FOREIGN PATENT DOCUMENTS

| DE | 2 208 293 | 8/1973 |
| DE | 27 49 957 A1 | 5/1978 |
| DE | 40 42 283 A1 | 7/1992 |
| JP | 07002733 A | 1/1995 |
| WO | WO 00/64876 | 11/2000 |

OTHER PUBLICATIONS

Bassoli et al, Quantitative Structure-Activity Relationships of Sweet Isovanillyl Derivatives, Quant. Struct.-Act. Relat., vol. 20, 2001, pp. 3-16.
Fields E. K., Synthesis of 2-Carboxybenzyl Aryl Ethers, J. Chem. Soc., 1964, pp. 4074-4075.
Ghera et al, Annulation Ractions Leading to Naphthalene Derivatives. New Syntheses of Natural 1,2- and 1,4-Naphthoquinones, J. Org. Chem., vol. 50, 1985, pp. 3355-3359.

* cited by examiner

*Primary Examiner*—Shailendra Kumar
*Assistant Examiner*—Jennifer Cho
(74) *Attorney, Agent, or Firm*—Barbara E. Kurys

(57) ABSTRACT

The invention relates to a process for the preparation of a compound of the general formula (I) in which a) a compound (II) is reacted in the presence of a base B1 with a compound (III) and

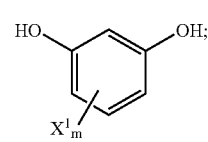

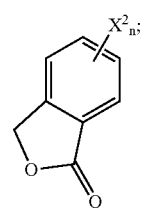

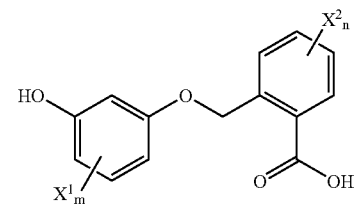

b) the compound (IV) formed as intermediate in step a) is reacted in the presence of a base B2 with a compound (V) to give the compound of the general formula (I)

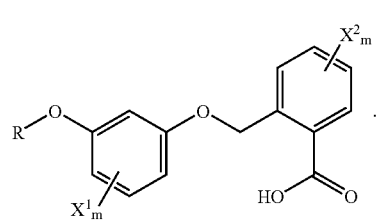

11 Claims, No Drawings

PROCESS FOR THE PREPARATION OF SUBSTITUTED 2-(PHENOXYMETHYL) BENZOIC ACIDS

The invention relates to a process for the preparation of substituted 2-(phenoxymethyl)-benzoic acids of the general formula (I). The present invention further relates to novel intermediates which are formed in the process according to the invention for the preparation of the compounds of the general formula (I).

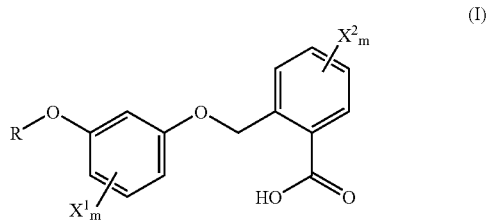

(I)

Compounds of the general formula (I) are suitable as medicaments, for example for lowering blood lipids and for the treatment of diabetes, because they have a large pharmacological effect as agonist or antagonist of the peroxisome proliferator-activated receptor (PPAR).

A large number of PPAR agonists and antagonists has been disclosed in WO 00/64876, including the compounds of the general formula (I).

The process described in WO 00/64876 for the preparation of compounds of the general formula (I) has, however, some disadvantages, also in relation to an industrial preparation of these compounds of pharmacological interest. In this preparation method, resorcinol is reacted with 2-bromomethylbenzoic esters, after which the intermediate containing a free OH group is reacted with an alkylating reagent in the presence of the base potassium carbonate, and finally compounds of the formula I are obtained by hydrolysis of the ester. The particular problem in this process is the precursor 2-bromomethylbenzoic ester, because this substance is thermally unstable and decomposes even at room temperature with cyclization and elimination of methyl bromide to give the corresponding phthalide, and is in addition highly lachrymatory and potentially carcinogenic and moreover can be prepared pure only by means of chromatography. A further disadvantage is that N-bromosuccinimide and the explosive dibenzoyl peroxide are employed in the process described in WO 00/64876 for the preparation of the precursor (2-bromomethylbenzoic ester). An alternative possibility for preparing the precursor is also by photochemical bromination as described in J. Org. Chem. 1985, 50, 3355-3359. There are always problems with such bromination reactions for the preparation of the precursor if the appropriate benzoic ester has alkyl groups in addition to that in position 2, because these can likewise be brominated. For example, some compounds of pharmacological interest of the formula (I) have a 6-methylbenzoic acid fragment, so that industrial preparation of such compounds by the aforementioned process would also be associated with distinctly higher costs as a result of the additional purification steps owing to the nonselective bromination.

Alternatives to the process described in WO 00/64876 for the preparation of 2-carboxybenzyl aryl ethers have been disclosed. Thus, all the alternatives are based on the process described in J. Chem. Soc. 1964, 4074-4075, in which phenol is reacted with the appropriate phthalide in the presence of the base sodium hydroxide at temperatures above 170° C. Thus, U.S. Pat. No. 5,221,762 relates to a process for the preparation of E-oxime ethers of phenylglyoxylic esters, where 2-carboxybenzyl aryl ethers are formed as intermediate. The aryl fragment may in this case be phenyl which is meta-substituted by $C_1$-$C_4$-alkoxy. The intermediate is prepared in the presence of a base at temperatures between 50° C. and 250° C. in the melt. Correspondingly, in DE-A 2 208 893, the preparation of tricyclic α-oxy carboxylic acid derivatives starts from the precursor guaiacol, with addition of a methoxide solution being followed firstly by removing the solvent methanol by distillation and, after addition of the phthalide, heating the reaction mixture at 180 to 190° C.

It is not absolutely necessary to prepare 2-carboxybenzyl aryl ethers in the melt; on the contrary, higher-boiling solvents can also be employed where appropriate. DE-A 27 49 957 describes a process for the preparation of quinolizidylidene derivatives of xanthenes, thioxanthenes and dibenzoxepines in which 4-methylphenol is reacted with phthalide using sodium hydride as base and dimethylformamide as solvent under reflux. Analogously, JP-A 07002733 describes the preparation of 2-carboxybenzyl aryl ethers using alcoholates as base and higher boiling solvents. The aryl fragment may, inter alia, also be a phenyl which is substituted in the meta position by lower alkoxy.

It is common to all the processes described above for the preparation of 2-carboxybenzyl aryl ethers that the reaction of the alcohol with the phthalide must take place at high temperatures (at least 100° C.) because, otherwise, only little or no reaction takes place. An additional finding is that in no case is resorcinol or a derivative thereof with two free hydroxyl groups employed. Where the phenols used have additional alkoxy substituents (not only in the meta position), these are unsubstituted lower alkoxy substituents. The PPAR agonists and antagonists of the general formula (I) described in WO 00/64876 are, however, compounds which have as radical R preferably arylalkyl or heteroarylalkyl substituents which in turn may be substituted one or more times. The radicals R thus predominantly have a moderate to large molecular weight. A process analogous to, for example, JP-A 07002733 cannot, however, be employed to prepare compounds of formula I because the ether linkage between R and the phenyl fragment of the alcohol is unstable because of the high temperatures necessary for the reaction of alcohol and phthalide. A higher temperature and a higher molecular weight of the corresponding substituent R mean a smaller yield of compounds of the general formula (I).

Accordingly, the object on which the invention is based is to provide a process for the preparation of PPAR agonists and antagonists of the general formula (I), which process does not have the disadvantages of those disclosed in the prior art.

The object is achieved by a process for the preparation of a compound of the general formula (I), wherein a) a compound (II) is reacted in the presence of a base B1 with a compound (III) and

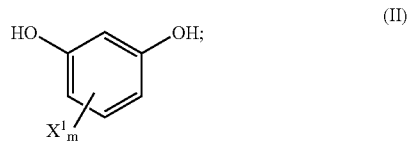

(II)

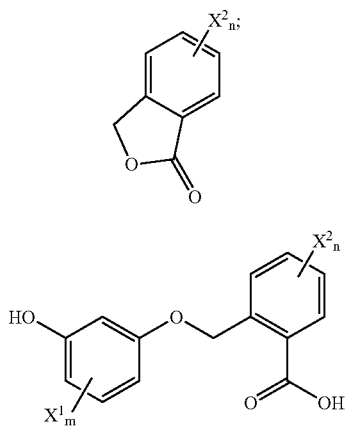
(III)

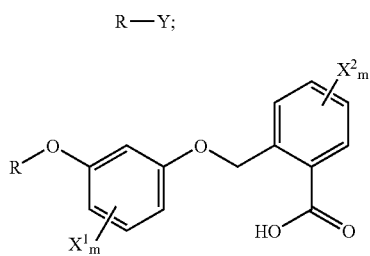
(IV)

b) the compound (IV) formed as intermediate in step a) is reacted in the presence of a base B2 with a compound (V) to give the compound of the general formula (I)

R—Y;  (V)

(I)

in which:

R is selected from the group consisting of:

unsubstituted or at least monosubstituted $C_1$-$C_{10}$-alkyl, heterocyclyl, aryl-($C_1$-$C_{10}$-alkyl)-, heteroaryl-($C_1$-$C_{10}$-alkyl)- and heterocyclyl-($C_1$-$C_{10}$-alkyl)-, where the substituents are selected from halogen, $C_1$-$C_6$-alkyl, —O-aryl, oxo, $C_1$-$C_6$-alkoxy, —C(O)O—($C_1$-$C_6$-alkyl), $C_2$-$C_6$-alkenyl, $C_2$-$C_6$-alkynyl, —C(O)—($C_1$-$C_6$-alkyl), -C(O)NH$_2$, —C(O)NH($C_1$-$C_6$-alkyl), —C(O)N($C_1$-$C_6$-alkyl)$_2$, —S—($C_1$-$C_6$-alkyl), —SO$_2$, —SO$_2$($C_1$-$C_6$-alkyl), —NH$_2$, —N($C_1$-$C_6$-alkyl)$_2$, —NH($C_1$-$C_6$-alkyl), —NO$_2$, —CN, trifluoromethyl, trifluoromethoxy, aryl, heterocyclyl and heteroaryl, and aryl, heterocyclyl and heteroaryl may in turn be at least monosubstituted by $C_1$-$C_3$-alkyl, $C_1$-$C_3$-alkoxy, halogen or trifluoromethyl;

$X^1$ is halogen, $C_1$-$C_6$-alkyl, $C_1$-$C_6$-alkoxy, trifluoromethyl, aryl, heterocyclyl or heteroaryl, where aryl, heterocyclyl and heteroaryl may in turn be at least monosubstituted by $C_1$-$C_3$-alkyl, $C_1$-$C_3$-alkoxy, halogen or trifluoromethyl;

$X^2$ is halogen, $C_1$-$C_6$-alkyl, $C_1$-$C_6$-alkoxy, trifluoromethyl, aryl, heterocyclyl or heteroaryl, where aryl, heterocyclyl and heteroaryl in turn may be at least monosubstituted by $C_1$-$C_3$-alkyl, $C_1$-$C_3$-alkoxy, halogen or trifluoromethyl;

heteroaryl is a 5- to 14-membered, aromatic, mono-, bi- or tricyclic heterocycle which contains one or more heteroatoms selected from N, O and S;

aryl is a 6- to 14-membered, aromatic mono-, bi- or tricyclic system;

heterocyclyl is a 5- to 14-membered, nonaromatic, mono-, bi- or tricyclic heterocycle which contains one or more heteroatoms selected from N, O and S;

m is 0, 1, 2, 3 or 4;

n is 0, 1, 2, 3 or 4;

Y is a leaving group and

B2 is an alkali metal hydroxide, alkaline earth metal hydroxide, alkali metal alcoholate, alkaline earth metal alcoholate, alkali metal hydride, alkaline earth metal hydride, silazide, alkali metal amide or alkaline earth metal amide.

The process according to the invention has the advantages compared with those of the state of the art that uniform products of compounds of the general formula (I) can be prepared in high yields and/or with few intermediate stages, which is economically worthwhile in particular in relation to industrial utilization. Compared with the processes described in WO 00/64876, on the one hand the use of carcinogenic and unstable intermediate compounds is dispensed with and, in addition, the free benzoic acid can be employed in the alkylation reaction in step b) owing to suitable choice of the base. This saves two synthetic steps because it is necessary in the processes described in WO 00/64876 for the free benzoic acid first to be protected in the form of a suitable ester and to be deprotected again in the final reaction stage. The advantage of the essential reversal of reaction steps a) and b) compared with the processes like those described for example in JP-A 07002733 (coupling of meta-lower alkoxyphenols with phthalide) is that it is possible in this way to prepare compounds of the formula (I) for the very first time or in economically worth-while yields, because the alkylation reaction carried out in step b) of the process according to the invention can be carried out at distinctly lower temperatures than the ether linkage performed in step a).

The process according to the invention can be used to prepare compounds of the general formula (I)

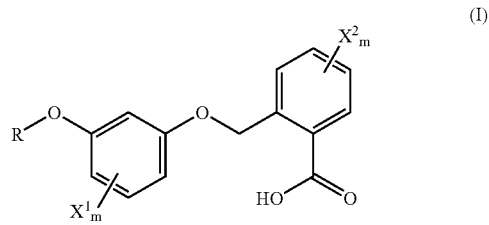
(I)

in which:

R is selected from the group consisting of:

unsubstituted or at least monosubstituted $C_1$-$C_{10}$-alkyl, heterocyclyl, aryl-($C_1$-$C_{10}$-alkyl)-, heteroaryl-($C_1$-$C_{10}$-alkyl)- and heterocyclyl-($C_1$-$C_{10}$-alkyl)-, where the substituents are selected from halogen, $C_1$-$C_6$-alkyl, —O-aryl, oxo, $C_1$-$C_6$-alkoxy, $C_2$-$C_6$-alkenyl, $C_2$-$C_6$-alkynyl, —C(O)—($C_1$-$C_6$-alkyl), —C(O)NH$_2$, —C(O)NH($C_1$-$C_6$-alkyl),-C(O)N($C_1$-$C_6$-alkyl)$_2$, —S—($C_1$-$C_6$-alkyl), —SO$_2$NH$_2$, —SO$_2$—($C_1$-$C_6$-alkyl), —NH$_2$, —N($C_1$-$C_6$-alkyl)$_2$, —NH($C_1$-$C_6$-alkyl), —NO$_2$, —CN, trifluoromethyl, trifluoromethoxy, aryl, heterocyclyl and heteroaryl, and aryl, heterocyclyl and heteroaryl may in turn be at least monosubstituted by $C_1$-$C_3$-alkyl, $C_1$-$C_3$-alkoxy, halogen or trifluoromethyl;

$X^1$ is halogen, $C_1$-$C_6$-alkyl, $C_1$-$C_6$-alkoxy, trifluoromethyl, aryl, heterocyclyl or heteroaryl, where aryl, heterocyclyl and heteroaryl may in turn be at least monosubstituted by $C_1$-$C_3$-alkyl, $C_1$-$C_3$-alkoxy, halogen or trifluoromethyl;

$X^2$ is halogen, $C_1$-$C_6$-alkyl, $C_1$-$C_6$-alkoxy, trifluoromethyl, aryl, heterocyclyl or heteroaryl, where aryl, heterocyclyl and heteroaryl in turn may be at least monosubstituted by $C_1$-$C_3$-alkyl, $C_1$-$C_3$-alkoxy, halogen or trifluoromethyl;

heteroaryl is a 5- to 14-membered, aromatic, mono-, bi- or tricyclic heterocycle which contains one or more heteroatoms selected from N, O and S;

aryl is a 6- to 14-membered, aromatic mono-, bi- or tricyclic system;

heterocyclyl is a 5- to 14-membered, nonaromatic, mono-, bi- or tricyclic heterocycle which contains one or more heteroatoms selected from N, O and S;

m is 0, 1, 2, 3 or 4;

n is 0, 1, 2, 3 or 4.

Where groups, fragments, radicals or substituents such as, for example, aryl, heteroaryl, alkyl, alkoxy etc. are present more than once in the compounds of the formula (I), they all have, independently of one another, the meanings listed above and may thus in each (individual) case have either an identical or a mutually independent meaning. The following statements apply to (for example) aryl and every other radical irrespective of whether it is referred to as aryl group, substituent, fragment or radical. For example, in a di($C_1$-$C_6$-alkyl)amino group, the two alkyl substituents may be either identical or different (for example 2× ethyl or 1× propyl and 1× hexyl).

Where a substituent, for example aryl, in the above definitions of compounds of formula (I) may be unsubstituted or at least monosubstituted by a group of further substituents, for example $C_1$-$C_6$-alkyl, $C_1$-$C_6$-alkoxy, halogen etc., the selection from the series of further substituents in the cases where aryl is polysubstituted takes place independently of one another. Thus, for example when aryl is disubstituted, all combinations of the further substituents are included. Aryl may thus be, for example, disubstituted by ethyl, aryl may in each case be monosubstituted by methyl and ethoxy, aryl may in each case be monosubstituted by ethyl and fluorine, aryl may be disubstituted by methoxy, etc.

Alkyl radicals may be either linear or branched, acyclic or cyclic. This also applies when they are part of another group such as, for example, alkoxy groups ($C_1$-$C_{10}$-alkyl-O-), alkoxycarbonyl groups or amino groups or if they are substituted.

Examples of alkyl groups are: methyl, ethyl, propyl, butyl, pentyl, hexyl, heptyl, octyl, nonyl or decyl. Included therein are the n-isomers of these radicals and isopropyl, isobutyl, isopentyl, sec-butyl, tert-butyl, neopentyl, 3,3-dimethylbutyl etc. Unless described otherwise, the term alkyl additionally includes alkyl radicals which are unsubstituted or optionally substituted by one or more further radicals, for example 1, 2, 3 or 4 identical or different radicals such as, for example, aryl, heteroaryl, alkoxy or halogen. It is moreover possible for the additional substituents to occur in any position of the alkyl radical. The term alkyl also includes cycloalkyl and cycloalkylalkyl (alkyl which in turn is substituted by cycloalkyl), where cycloalkyl has at least 3 carbon atoms. Examples of cycloalkyl radicals are: cyclopropyl, cyclobutyl, cyclopentyl, cyclohexyl, cycloheptyl, cyclooctyl, cyclononyl and cyclodecyl. Polycyclic ring systems are also possible where appropriate, such as decalinyl, norbornanyl, bornanyl or adamantanyl. The cycloalkyl radicals may be unsubstituted or optionally substituted by one or more further radicals as listed above by way of example for the alkyl radicals.

Examples of alkenyl and alkynyl groups are: vinyl, 1-propenyl, 2-propenyl (allyl), 2-butenyl, 2-methyl-2-propenyl, 3-methyl-2-butenyl, ethynyl, 2-propynyl (propargyl), 2-butynyl or 3-butynyl. The term alkenyl here expressly includes cycloalkenyl radicals and cycloalkenylalkyl radicals (alkyl substituted by cycloalkenyl) containing at least three carbon atoms. Examples of cycloalkenyl are: cyclopentenyl, cyclohexenyl, cycloheptenyl and cyclooctenyl.

The alkenyl radicals may have one to three conjugated or unconjugated double bonds (i.e. also alk-dienyl and alk-trienyl radicals), preferably one double bond in a linear or branched chain, and the same applies to the triple bonds for alkynyl radicals. The alkenyl and alkynyl radicals may be unsubstituted or optionally substituted by one or more further radicals as listed above by way of example for the alkyl radicals.

Unless stated otherwise, the aforementioned aryl, heteroaryl and heterocyclyl radicals may be both unsubstituted and have one or more, for example 1, 2, 3 or 4, further of the aforementioned substituents in any position. For example, the substituent in monosubstituted phenyl radicals may be in position 2, 3 or 4, and the substituents in disubstituted phenyl radicals may be in the 2,3 position, 2,4 position, 2,5 position, 2,6 position, 3,4 position or 3,5 position. The substituents in trisubstituted phenyl radicals may be in the 2,3,4 position, 2,3,5 position, 2,3,6 position, 2,4,5 position, 2,4,6 position or 3,4,5 position. The substituents in tetrasubstituted phenyl radicals may be in the 2,3,4,5 position, the 2,3,4,6 position or in the 2,3,5,6 position.

The definitions mentioned above and hereinafter relating to monovalent radicals apply equally to divalent radicals such as phenylene, naphthylene or heteroarylene. These divalent radicals (fragments) may be linked with the adjacent groups via any ring carbon atom. In the case of phenylene radicals, this may be in the 1,2 position (ortho-phenylene), 1,3 position (meta-phenylene) or 1,4 position (para-phenylene). In the case of a 5-membered aromatic system containing a heteroatom, such as, for example, thiophene or furan, the two free bonds may be in the 2,3 position, 2,4 position, 2,5 position or 3,4 position. A divalent radical derived from a 6-membered aromatic system having one heteroatom, such as, for example, pyridine, may be a 2,3, 2,4, 2,5, 2,6, 3, 4 or 3,5 pyridinediyl radical. In the case of unsymmetrical divalent radicals, the present invention also includes all positional isomers, i.e. in the case for example of a 2,3-pyridinediyl radical the compound in which one adjacent group is in position 2 and the other adjacent group is in position 3 is just as much included as the compound in which one adjacent group is in position 3 and the other adjacent group is in position 2.

Unless stated otherwise, heteroaryl radicals, heteroarylene radicals, heterocyclyl radicals and heterocyclylene radicals, and rings formed by two groups bonded to nitrogen, are preferably derived from completely saturated, partially or wholly unsaturated heterocycles (i.e. heterocycloalkanes, heterocycloalkenes, heteroaromatic compounds), which contain 1, 2, 3 or 4 heteroatoms which may be both different and identical. They are preferably derived from heterocycles which contain 1, 2 or 3, particularly preferably 1 or 2, heteroatoms which may be identical or different. Unless stated otherwise, the heterocycles are mono- or polycyclic, for example monocyclic, bicyclic or tricyclic. They are preferably monocyclic or bicyclic. Preference is given to 5-membered, 6-membered and 7-membered rings, particularly preferably 5-membered and 6-membered rings. In the case of polycyclic heterocycles having 2 or more heteroatoms, these may all be in the same ring or be distributed over a plurality of rings.

Radicals referred to as heteroaryl in the present invention are those derived from monocyclic, bicyclic or tricyclic aromatic heterocycles. Examples of heteroaryl are: pyrrolyl, furanyl (furyl), thiophenyl (thienyl), imidazolyl, pyrazolyl, 1,2,3-triazolyl, 1,2,4-triazolyl, 1,3-oxazolyl (oxazolyl), 1,2-oxazolyl (isoxazolyl), oxadiazolyl, 1,3-thiazolyl (thiazolyl), 1,2-thiazolyl (isothiazolyl), tetrazolyl, pyridinyl (pyridyl) pyridazinyl, pyrimidinyl, pyrazinyl, 1,2,3-triazinyl, 1,2,4-triazinyl, 1,3,5-triazinyl, 1,2,4,5-tetrazinyl, indazolyl, indolyl, benzothiophenyl, benzofuranyl, benzothiazolyl, benzimidazolyl, benzodioxolyl, acridinyl, quinolinyl, isoquinolinyl, quinazolinyl, quinoxalinyl, phthalazinyl, thienothiophenyl, 1,8-naphthyridinyl, other naphthyridinyls, pteridinyl or phenothiazinyl. Where the systems are not monocyclic, also included for each of the aforementioned heteroaryls for each additional ring is the saturated form (perhydro form) or the partially unsaturated form (for example the dihydro form or tetrahydro form) or the maximally unsaturated (nonaromatic) form where the respective forms are known and stable. The term heteroaryl thus includes in the present invention for example bicyclic radicals in which both the two rings are aromatic and bicyclic radicals in which only one ring is aromatic. Such examples of heteroaryl are: 3H-indolinyl, 2(1H)-quinolinonyl, 4-oxo-1,4-dihydroquinolinyl, 2H-1-oxoisoquinolyl, 1,2-dihydroquinolinyl, (2H)quinolinyl N-oxide, 3,4-dihydroquinolinyl, 1,2-dihydroisoquinolinyl, 3,4-dihydroisoquinolinyl, chromonyl, 3,4-dihydroisoquinoxalinyl, 4-(3H)quinazolinonyl, 4H-chromenyl, 4-chromanonyl, oxindolyl, 1,2,3,4-tetrahydroisoquinolinyl, 1,2,3,4-tetrahydroquinolinyl, 1H-2,3-dihydroisoindolyl, 2,3-dihydrobenzo[f]isoindolyl, 1,2,3,4- tetrahydrobenzo[g]isoquinolinyl, 1,2,3,4 - tetrahydrobenzo[g]isoquinolinyl, chromanyl, isochromanonyl, 2,3-dihydrochromonyl, 1,4-benzodioxanyl, 1,2,3,4-tetrahydroquinoxalinyl, 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-dihydrobenzoxazolyl, 1,4-naphthoquinolyl, 5,6,7,8-tetrahydroquinolinyl, 5,6,7,8-tetrahydroisoquinoxalinyl, 5,6,7,8-tetrahydroquinoxalinyl, 5,6,7,8-tetrahydroquinolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizolo-[4,5]-pyridin-2-onyl, 2,3-dihydro-1,4-dinaphthoquinonyl, 2,3-dihydro-1H-pyrrol[3,4-b]quinolinyl, 1,2,3,4-tetrahydrobenzo[b][1,7]naphthyridinyl, 1,2,3,4-tetrahydrobenz[b][1,6]naphthyridinyl, 1,2,3,4-tetrahydro-9H-pyrido[3,4-b]indolyl, 1,2,3,4-tetrahydro-9H-pyrido[4,3-b]indolyl, 2,3-dihydro-1H-pyrrolo[3,4-b]indolyl, 1H-2,3,4,5-tetrahydroazepino[3,4-b]indolyl, 1H-2,3,4,5-tetrahydroazepino[4,3-b]indolyl, 1H-2,3,4,5-tetrahydroazepino[4,5-b]indolyl, 5,6,7,8-tetrahydro[1,7]napthyridinyl, 1,2,3,4-tetrahydro[2,7]naphthyridyl, 2,3-dihydro[1,4]dioxino[2,3-b]pyridyl, 2,3-dihydro[1,4]dioxino-[2,3-b]pryidyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]napthyridinyl, 1,2,3,4-tetrahydro[1,6]napthyridinyl, 1,2,3,4-tetrahydro[1,7]napthyridinyl, 1,2,3,4-tetrahydro[1,8]napthyridinyl or 1,2,3,4-tetrahydro[2,6]napthyridinyl.

Radicals referred to as heterocyclyl in the present invention are those derived from monocyclic, bicyclic or tricyclic nonaromatic heterocycles. Nonaromatic heterocycles mean hereinafter in particular heterocycloalkanes (completely saturated heterocycles) and heterocycloalkenes (partially unsaturated heterocycles). In the case of the heterocycloalkenes, also included are compounds having two or more double bonds which may also where appropriate be conjugated together. Examples of heterocyclyl are: pyrrolidinyl, piperidinyl, piperazinyl, imidazolidinyl, pyrazolidinyl, isothiazolidinyl, thiazolidinyl, isoxazolidinyl, oxazolidinyl, tetrahydrofuranyl, tetrahydrothiophenyl 1,3-dioxolanyl, 1,4-dioxinyl, pyranyl, thiopyranyl, 1,4-dioxinyl, 1,2-oxazinyl, 1,3-oxazinyl, 1,4-oxazinyl, 1,2-thiazinyl, 1,3-thiazinyl, 1,4-thiazinyl, azepinyl, 1,2-diazepinyl, 1,3-diazepinyl, 1,4-diazepinyl, 1,3-oxazepinyl, 1,3-thiazepinyl, 2-oxo-azepanyl, morpholinyl, thiomorpholinyl, 1,2,3,4-tetrahydropyridinyl, 1,2-dihydropyridinyl, 1,4-dihydropyridinyl, 1,2,3,6-tetrahydropyridinyl, 4(3H)-pyrimidonyl, 1,4,5,6-tetrahydropyrimidinyl, 2-pyrrolinyl, 3-pyrrolinyl, 2-imidazolinyl, 2-pyrazolinyl, 3,4-dihydro-2H-pyranyl, dihydrofuranyl, 7-oxabicyclo[2.2.1]heptenyl, dihydrothiophenyl and dihydrothiopyranyl. The degree of saturation of heterocyclic groups is indicated in the definition in each case.

Substituents derived from these heterocycles may be linked via any suitable carbon atom, and be provided with further substituents. Radicals derived from nitrogen-containing heterocycles may have a hydrogen atom or another substituent on the appropriate nitrogen atom. Examples include pyrrole, imidazole, pyrrolidine, morpholine, piperazine residues etc. These nitrogen-containing heterocyclic radicals may also be bonded via the ring nitrogen atom, especially when the relevant heterocyclic radical is bonded to a carbon atom. For example, a thienyl radical may be in the form of 2-thienyl or 3-thienyl, and a piperidinyl radical in the form of 1-piperidinyl (piperidino), 2-piperidinyl, 3-piperidinyl or 4-piperidinyl. Suitable nitrogen-containing heterocycles may also be in the form of N-oxides or of quarternary salts which have a counter ion which is derived from a physiologically acceptable acid. For example, pyridyl radicals may be in the form of pyridine N-oxides. Suitable sulfur-containing heterocycles may also be in the form of S-oxide or S,S-dioxide.

Radicals referred to as aryl in the present invention are those derived from monocyclic, bicyclic or tricyclic aromatic systems which contain no ring heteroatoms. Where the systems are not monocyclic, the term aryl includes for each additional ring also the saturated form (perhydro form) or the partially unsaturated form (for example the dihydro form or tetrahydro form) or the maximally unsaturated (nonaromatic) form where the respective forms are known and stable. The term aryl also includes in the present invention for example bicyclic radicals in which both the two rings are aromatic and bicyclic radicals in which only one ring is aromatic. Examples of aryl are: phenyl, naphthyl, anthracyl, indanyl, 1,2-dihydronaphthyl, 1,4-dihydronaphthyl, indenyl, 1,4-naphthoquinonyl or 1,2,3,4-tetrahydronaphthyl.

Arylalkyl means that an alkyl radical is substituted in turn by an aryl radical. Heteroarylalkyl means that an alkyl radical is substituted in turn by a heteroaryl radical. Heterocyclylalkyl means that an alkyl radical is substituted in turn by a heterocyclyl radical. For the definitions and possible substitutions of alkyl, heteroaryl, heterocyclyl and aryl, reference is made to the definitions above.

Halogen is fluorine, chlorine, bromine or iodine, with preference for fluorine, chlorine or bromine, and particular preference for fluorine or chlorine.

Preferred compounds of the general formula (I) which can be prepared by the process according to the invention are defined as follows:

R is selected from the group consisting of:

unsubstituted or at least monosubstituted $C_1$-$C_{10}$-alkyl, heterocyclyl, aryl-($C_1$-$C_{10}$-alkyl)-, heteroaryl-($C_1$ and heterocyclyl-($C_1$-$C_{10}$-alkyl)-, where the substituents are selected from halogen, $C_1$-$C_6$-alkyl, —O-aryl, oxo, $C_1$-$C_6$-alkoxy, —C(O)O—($C_1$-$C_6$-alkyl), $C_2$-$C_6$-alkenyl, $C_2$-$C_6$-alkynyl, —C(O)—($C_1$-$C_6$-alkyl), —C(O)NH$_2$, —C(O)NH($C_1$-$C_6$-alkyl), —C(O)N($C_1$-$C_6$-alkyl)$_2$, —S—($C_1$-$C_6$-alkyl), —SO$_2$NH$_2$, —SO$_2$-($C_1$-$C_6$-alkyl), —NH$_2$, —N($C_1$-$C_6$-alkyl)$_2$, —NH($C_1$-$C_6$-alkyl), —NO$_2$, —CN, trifluoromethyl, trifluoromethoxy, aryl, heterocyclyl and heteroaryl, and aryl, heterocyclyl and heteroaryl in turn may be at least monosubstituted by $C_1$-$C_3$-alkyl, $C_1$-$C_3$-alkoxy, halogen or trifluoromethyl;

$X^1$ is halogen, $C_1$-$C_6$-alkyl, $C_1$-$C_6$-alkoxy or trifluoromethoxy;

$X^2$ is halogen, $C_1$-$C_6$-alkyl, $C_1$-$C_6$-alkoxy or trifluoromethoxy;

heteroaryl is a 5- to 14-membered, aromatic, mono-, bi- or tricyclic heterocycle which contains one or more heteroatoms selected from N, O and S;

aryl is a 6- to 14-membered, aromatic mono-, bi- or tricyclic system;

heterocyclyl is a 5- to 14-membered, nonaromatic, mono-, bi- or tricyclic heterocycle which contains one or more heteroatoms selected from N, O and S;

m is 0, 1 or 2;

n is 0, 1 or 2.

More preferred compounds of the general formula (I) are defined as follows:

R is selected from the group consisting of:

unsubstituted or at least monosubstituted aryl-($C_1$-$C_6$-alkyl)- and heteroaryl-($C_1$-$C_6$-alkyl)-, where the substituents are selected from halogen, $C_1$-$C_4$-alkyl, —O-aryl, oxo, $C_1$-$C_4$-alkoxy, aryl, heterocyclyl and heteroaryl, and aryl, heterocyclyl and heteroaryl may in turn be at least monosubstituted by $C_1$-$C_3$-alkyl, $C_1$-$C_3$-alkoxy, halogen or trifluoromethyl;

$X^1$ is halogen, $C_1$-$C_6$-alkyl, $C_1$-$C_6$-alkoxy or trifluoromethoxy;

$X^2$ ist halogen, $C_1$-$C_6$-alkyl, $C_1$-$C_6$-alkoxy or trifluoromethoxy;

heteroaryl is a 5- to 14-membered, aromatic, mono-, bi- or tricyclic heterocycle which contains one or more heteroatoms selected from N, O and S;

aryl is a 6- to 14-membered, aromatic mono-, bi- or tricyclic system;

heterocyclyl is a 5-bis 14-membered, nonaromatic, mono-, bi- or tricyclic heterocycle which contains one or more heteroatoms selected from N. O and S;

m is 0, 1 or 2;

n is 0, 1 or 2.

Even more preferred compounds of the general formula (I) are defined as follows:

R is selected from the group consisting of:

unsubstituted or at least monosubstituted aryl-($C_1$-$C_6$-alkyl)- and heteroaryl-($C_1$-$C_6$-alkyl)-, where the substituents are slected from halogen, $C_1$-$C_4$-alkyl, —O-aryl, oxo, $C_1$-$C_4$-alkoxy, aryl, heterocyclyl and heteroaryl, and aryl, heterocyclyl and heteroaryl may in turn be at least monosubstituted by $C_1$-$C_3$-alkyl, $C_1$-$C_3$-alkoxy, halogen or trifluoromethyl;

$X^1$ is halogen, $C_1$-$C_6$-alkyl, $C_1$-$C_6$-alkoxy or trifluoromethoxy;

$X^2$ is halogen, $C_1$-$C_6$-alkyl, $C_1$-$C_6$-alkoxy or trifluoromethoxy;

heteroaryl is a 5- to 10-membered, aromatisc, mono- or bicyclic heterocycle which contains one or more heteroatoms selected from N, O and S;

aryl is phenyl, naphthyl, indanyl, dihydronaphthyl, tetrahydronaphthyl or indenyl;

heterocyclyl is pyrrolidinyl, piperidinyl, piperazinyl, tetrahydrofuranyl or morpholinyl;

m is 0, 1 or 2;

n is 0, 1 or 2;

Particularly preferred compounds of the general formula (I) are defined as follows:

R is unsubstituted or at least monosubstituted benzyl or heteroarylmethyl, where the substituents are selected from fluorine, chlorine, $C_1$-$C_4$-alkyl, —O-phenyl, $C_1$-$C_4$-alkoxy, phenyl and heteroaryl, and phenyl and heteroaryl may in turn be at least monosubstituted by $C_1$-$C_3$-alkyl, $C_1$-$C_3$-alkoxy, chlorine or fluorine;

$X^1$ is $C_1$-$C_3$-alkyl or bromine;

$X^2$ is $C_1$-$C_3$-alkyl, fluorine or chlorine;

heteroaryl is oxazolyl, isoxazolyl, oxadiazolyl, thiazolyl, isothiazolyl, pyridinyl, pyridazinyl, pyrimidinyl, pyrazinyl, indolyl, benzimidazolyl, quinolinyl, isoquinolinyl, quinazolinyl or quinoxalinyl;

m is 0 or 1;

n is 0, 1 or 2.

Very particularly preferred compounds of the general formula (I) are defined as follows:

R is unsubstituted or at least monosubstituted benzyl or heteroarylmethyl, where the substituents are selected from fluorine, chlorine, $C_1$-$C_4$-alkyl, phenyl and heteroaryl, and phenyl and heteroaryl may in turn be at least monosubstituted by $C_1$-$C_3$-alkyl, chlorine or fluorine;

$X^2$ is $C_1$-$C_3$-alkyl;

heteroaryl is oxazolyl or isoxazolyl;

m is 0;

n is 0 or 1.

Step a) of the Process According to the Invention:

In step a) of the process according to the invention, a compound (II) is reacted in the presence of a base B1 with a compound (III) to form a compound (IV).

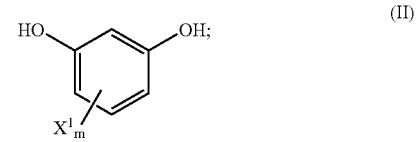

(II)

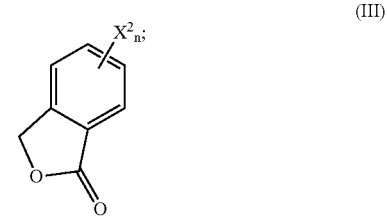

(III)

-continued

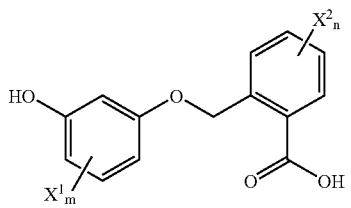

(IV)

The compounds of the formulae (II) and (III) have the corresponding definitions of the general formula (I). Compounds suitable as compound (II), which are referred to hereinafter as resorcinol derivatives, are only those having two hydroxyl groups in meta position relative to one another. The corresponding hydroquinone and catechol derivatives cannot, however, be used in the process according to the invention because they react to only a small extent or not all with the compounds of the formula (III), which are referred to hereinafter as phthalides.

Bases suitable as bases B1 are in principle all those familiar to the skilled worker. Preferably suitable are alkali metal and alkaline earth metal alcoholates such as sodium methoxide, potassium methoxide and potassium tert-butoxide. Equally suitable are silazides such as potassium hexamethyldisilazide and lithium hexamethyldisilazide. The compounds of the formula (IV) can likewise be prepared using alkali metal hydroxides such as sodium hydroxide and potassium hydroxide, although the water resulting from the deprotonation likewise reacts with the phthalide employed, with ring opening which is irreversible under the reaction conditions, and thus sequesters the precursor from the desired reaction, resulting in losses of yield. Alkali metal alcoholates are particularly preferred as base B1, and sodium methoxide, potassium methoxide and potassium tert-butoxide are very particularly preferred.

Suitable solvents are solvents or mixtures thereof having a boiling point of >100° C., such as, for example, toluene, o-, m-, p-xylene, glyme, dimethylformamide, N-methyl-1-pyrrolidone and N,N-dimethylacetamide. N-Methyl-1-pyrrolidone and N,N-dimethylacetamide are particularly preferred.

The amount of base B1 to be employed should be equimolar in relation to the amount of resorcinol derivative (II) employed, with preference for the exactly equimolar amount. Excesses of base B1 should be avoided because, otherwise, both free hydroxyl groups of the compound (II) are alkylated.

Less than equimolar amounts of base B1 should likewise be avoided because this leads to reduced conversion, likewise having an adverse effect on the yield. The amount of base B1 and resorcinol derivative (II) employed must be at least equimolar in relation to the phthalide (III) employed. The reaction rate can be increased by simultaneous use of larger amounts of resorcinol derivative (II) and of base B1. A one- to six-molar excess of base B1 and resorcinol derivative (II), based on the amount of phthalide (III) employed, is preferably used.

Phthalide (III), resorincol derivative (II), base B1 and solvent are mixed at room temperature, the sequence of addition being immaterial and having no affect on the conversion in the reaction and the yield of isolated product. Accordingly, it is unnecessary, as described in some of the preceding documents, to carry out the deprotonation of the resorcinol derivative (II) with the base B1 used, possibly also to remove the corresponding acid of the base B1 employed, and subsequently to add the phthalide (III) and to heat.

In general, the reaction is carried out after mixing the reactants and solvent at a temperature in the range from 80 up to 200° C., preferably between 110 and 150° C. The reaction time depends on the phthalide (III) employed and its steric demands.

No special conditions in relation to pressure are necessary, and it is expedient to operate under atmospheric pressure.

After completion of the reaction, the reaction mixture is diluted with water. The water is preferably added at temperatures of >60° C. because solidification of the reaction mixture may not be preventable, depending on the concentration thereof. The resulting solution is acidified to liberate the compounds (IV), preferably with an inorganic acid such as hydrochloric acid or sulfuric acid. Methods known to the skilled worker are used for further working up.

The intermediates of the formula (IV), which have not previously been disclosed in the literature, can be obtained in high yields and excellent purities by the process according to the invention. On use of N-methyl-1-pyrrolidone and N,N-dimethylacetamide it is possible initially to obtained solvates of the compounds of the formula (IV) with varying contents of said solvents. Suitable processes, e.g. recrystallization or heating with water, can be used to reduce or entirely remove the contents of said solvents in the isolated product. Removal of the solvate envelope is unnecessary for further use of the intermediates (IV) in step b) of the process according to the invention.

The process according to the invention in step a) and/or step b) can be carried out both batchwise and continuously. In a continuous procedure, the reaction partners are passed for example through a pipe reactor or cascades of stirred vessels.

Step b) of the Process According to the Invention:

In step b), the compound (IV) formed as intermediate in step a) of the process according to the invention is reacted in the presence of a base B2 with a compound R-Y (V) to give the compound of the general formula (I).

The compound (IV) formed as intermediate in step a), and the compound (V) have the corresponding definitions of the general formula (I). A suitable leaving group Y in the compound (V) is any leaving group known to the skilled worker. Preferred for Y are chlorine, bromine, iodine, mesylates or tosylates, particularly preferably chorine, bromine or iodine.

Suitable bases B2 are alkali metal and alkaline earth metal hydroxides such as sodium and potassium hydroxides, alkali metal and alkaline earth metal alcoholates such as sodium methoxide, potassium methoxide and potassium tert-butoxide, alkali metal and alkaline earth metal hydrides such as sodium and calcium hydrides. Likewise suitable are silazides such as potassium hexamethyldisilazide and lithium hexamethyldisilazide, and generally alkali metal and alkaline earth metal amides; alkali metal alcoholates are preferred, and sodium alcoholates are particularly preferred. On use of the aforementioned bases B2 it is possible in step b) of the process according to the invention to achieve a selective alkylation of the hydroxyl group of the compound (IV) formed as intermediate in step a). Additional alkylation of the unprotected carboxyl group of the compound (IV) takes place to only a small extent or not at all.

Bases which have proved unsuitable are carbonate bases such as, for example, potassium carbonate. Owing to the inadequate basicity, even with large excesses only the carboxyl group is deprotonated, leading to selective, but undesired, alkylation of the acid function of the compounds of the formula I. This selective alkylation of the acid function is observed at lower temperatures, in particular at temperatures of less than or equal to 50° C.; presumably because of the simultaneous presence of a hydroxyl group and of a carboxyl group, the basicity of carbonate bases is inadequate at low temperatures. Carbonate bases such as potassium carbonate can also be used if the free carboxyl group is protected with a suitable protective group, for example an ester as described in WO 00/64876, before step b) of the process according to the invention is carried out, and is deprotected again following step b). Such an additional protection/deprotection of the free carboxyl group is also encompassed by the process according to the invention.

Suitable solvents are all solvents or mixtures thereof which are unable to react with the bases employed:

i) aprotic polar solvents such as acetone and carboxamides, preferably N-methyl-1-pyrrolidinone, N,N-dimethylacetamide and dimethylformamide, ii) protic polar solvents such as, for example, alcohols such as methanol, ethanol and tert-butanol.

Alcohols and carboxamides are preferred. Carboxamides are particularly preferred.

The amount of alkylating reagent R-Y of the formula (V) employed is in the range from 1.0 to 1.5 mole equivalents based on the compound (IV) employed, preferably between 1.0 and 1.25 mole equivalents. It is also possible where appropriate to employ more than 1.5 mole equivalents of R-Y. The amount of base B2 employed is at least twice the molar amount of compound (IV) employed, with preference for exactly twice the molar amount of base B2 in relation to compound (IV).

The reaction is carried out at temperatures in the range from 20 up to 60° C., preferably from 20 up to 50° C., particularly preferably between 20 and 25° C., depending on the solvent used. The temperatures required by carboxamides as solvents are generally lower than by alcohols as solvents. Step b) can also be carried out at temperatures above 60° C. where appropriate.

The compound (IV) is introduced into the solvent and then the base B1 is added. The mixture is stirred for at least five minutes until both hydroxyl groups have been completely deprotonated. The alkylating reagent R-Y of the formula (V) is then added.

No special conditions in relation to pressure are necessary; it is expedient to operate under atmospheric pressure.

After completion of the reaction, the reaction mixture is diluted for example with a solution of sodium chloride, potassium chloride or sodium bicarbonate. The resulting solution is extracted for example with ethyl acetate, whereupon the organic constituents in the reaction solution are transferred into the organic phase. The ethyl acetate phase is then extracted with water. The compounds of the general formula (I) are liberated by acidifying the aqueous phase, for example, preferably with an inorganic acid such as hydrochloric acid or sulfuric acid. Methods known to the skilled worker are used for further working up. The compounds of the formula (I) according to the invention are obtained in high yields and good purities.

The purity of the isolated compounds of the general formula (I) can be increased where appropriate by subsequent crystallization.

In a further embodiment of the present compounds it is possible to follow step b) by preparing by methods known to the skilled worker—where defined for $X^1$, $X^2$ or R—from (—C(O)O—($C_1$-$C_6$-alkyl)), (—S—($C_1$-$C_6$-alkyl)) and/or ($C_1$-$C_6$-alkoxy) substituents by elimination of alkyl the corresponding compounds of the general formula (I) substituted by carboxyl, —SH and/or —OH. These additional substituents may be present independently of one another one or more times. The free carboxyl, (—SH) and/or (—OH) substituents are preferably obtained by addition of acid. These additional substituents can, where appropriate, also be obtained from substituents other than ester, thioalkoxy or alkoxy substituents.

The starting materials, solvents, bases etc. used in the process according to the invention are all purchasable or can be prepared by methods known to the skilled worker.

A further aspect of the present invention are the compounds of the formula (IV) which can be obtained as intermediates in step a) of the process according to the invention.

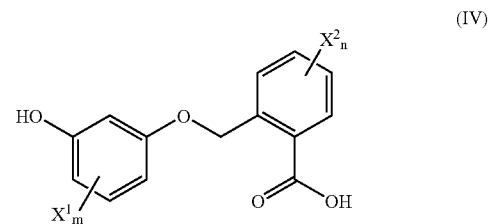

in which:

$X^1$ is halogen, $C_1$-$C_6$-alkyl, $C_1$-$C_6$-alkoxy, trifluoromethyl, aryl, heterocyclyl or heteroaryl, where aryl, heterocyclyl and heteroaryl may in turn be at least monosubstituted by $C_1$-$C_3$-alkyl, $C_1$-$C_3$-alkoxy, halogen or trifluoromethyl;

$X^2$ is halogen, $C_1$-$C_6$-alkyl, $C_1$-$C_6$-alkoxy, trifluoromethyl, aryl, heterocyclyl or heteroaryl, where aryl, heterocyclyl and heteroaryl may in turn be at least monosubstituted by $C_1$-$C_3$-alkyl, $C_1$-$C_3$-alkoxy, halogen or trifluoromethyl;

heteroaryl is a 5- to 14-membered, aromatic, mono-, bi- or tricyclic heterocycle which contains one or more heteroatoms selected from N, O and S;

aryl is a 6- to 14-membered, aromatic mono-, bi- or tricyclic system;

heterocyclyl is a 5- to 14-membered, nonaromatic, mono-, bi- or tricyclic heterocycle which contains one or more heteroatoms selected from N, O and S;

m is 0, 1, 2, 3 or 4;

n is 0, 1, 2, 3 or 4;

wherein 2-(3-hydroxy-4-methoxyphenoxymethyl)benzoic acid is excluded.

A compound being similar to those of the general formula (IV) is already known. U.S. Ser. No. 2003/0072842 A and A. Bassoli et al., Quant. Struct.-Act. Relat., 20(2001), p. 3-20 disclose the single compound 2(3-hydroxy-4-methoxyphenoxymethyl)benzoic acid. This compound is used as a sweetener, a connection to PPAR-agonists or -antagonists is not disclosed. Compounds as such, explicitly disclosed in U.S. Ser. No. 2003/0072842 A or by A. Bassoli et al., are not a subject of the present invention.

Preferred compounds of the formula (IV) have the following definition:

$X^1$ is halogen, $C_1$-$C_6$-alkyl, $C_1$-$C_6$-alkoxy or trifluoromethyl;

$X^2$ is halogen, $C_1$-$C_6$-alkyl, $C_1$-$C_6$-alkoxy or trifluoromethyl;

m is 0, 1, 2, 3 or 4;

n is 0, 1, 2, 3 or 4;

with the proviso that $X^1$=$C_1$-$C_6$-alkoxy is not in para-position to the ether-fragment.

More preferred compounds of the formula (IV) have the following definition:
$X^1$ is halogen, $C_1$-$C_6$-alkyl, $C_1$-$C_6$-alkoxy or trifluoromethyl;
$X^2$ is halogen, $C_1$-$C_6$-alkyl, $C_1$-$C_6$-alkoxy or trifluoromethyl;
m is 0 or 1;
n is 0, 1 or 2;
with the proviso that $X^1$=$C_1$-$C_6$-alkoxy is not in para-position to the ether-fragment.

Even more preferred compounds of the formula (IV) have the following definition:
$X^1$ is halogen, $C_1$-$C_3$-alkyl or trifluoromethyl;
$X^2$ is halogen, $C_1$-$C_3$-alkyl, $C_1$-$C_3$-alkoxy or trifluoromethyl;
m is 0 or 1;
n is 0, 1 or 2.

Particularly preferred compounds of the formula (IV) have the following definition:
$X^1$ is $C_1$-$C_3$-alkyl or bromine;
$X^2$ is $C_1$-$C_3$-alkyl, fluorine or chlorine;
m is 0 or 1;
n is 0, 1 or 2.

Very particularly preferred compounds of the formula (IV) have the following definition:
$X^2$ is $C_1$-$C_3$-alkyl;
m is 0;
n is 0 or 1.

As described above, the compounds of the formula (IV) can be prepared by step a) of the process according to the invention. They are suitable as starting compounds for synthesizing PPAR agonists and antagonists of general formula (I) by step b) of the process according to the invention.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

The following examples are intended to illustrate the process without, however, limiting it.

1. PREPATION OF THE COMPOUNDS OF THE FORMULA (IV)

EXAMPLE 1.1

2-(3-Hydroxyphenoxymethyl)-6-methylbenzoic Acid and the Solvates Thereof with N-methylpyrrolidone 2-(3-Hydroxyphenoxymethyl)-6-methylbenzoic Acid (Monosolvate with N-methylpyrrolidone)

7-Methylphthalide (30.1 g, 203 mmol), resorcinol (45.3 g, 407 mmol) and potassium tert-butoxide (47.6 g, 424 mmol) are suspended in 300 ml of N-methylpyrrolidone (NMP) and stirred at 140° C. for 21 h. After this time, a second amount of potassium tert-butoxide (2.4 g, 21.4 mmol) is added and stirring is continued at 140° C. for 2.5 h. The reaction mixture is cooled, 800 ml of water are added, and the mixture is acidified to pH=2 at 20° C. with concentrated hydrochloric acid. After stirring at 3 to 5° C. for 2 hours, the pale beige solid is filtered off with suction, washed with water and then dried. The isolated product contains 2-(3-hydroxyphenoxymethyl)-6-methylbenzoic acid and N-methylpyrrolidone as solvate molecule in a ratio of 1:1. Yield 77.7%, melting point 98 to 99° C.

$^1$H NMR (400 MHz, DMSO-d6)δ a) 2-(3-Hydroxyphenoxymethyl)-6-methylbenzoic Acid 13.3 (br s, 1H, COOH), 9.4 (br s 1H, OH), 7.34 (d, 1H) 7.33 (s, 1H), 7.25 (m, 1H 1H), 6.40-6.37 (2H), 5.04 (s, 2H, $CH_2$), 2.69 (s, 3H, $CH_3$)

b) N-Methylpyrrolidone 3.30 (t, 2H), 2.233 (s, 3H), 2.18 (t, 2H), 1.90 (m, 2H)

2-(3-Hydroxyphenoxymethyl)-6-methylbenzoic Acid (Hemisolvate with N-methylpyrrolidone)

53.5 g (150 mmol) of 2-(3-hydroxyphenoxymethyl)-6-methylbenzoic acid * NMP are dissolved in 250 ml of toluene with heating and cooled at 10 K/h to room temperature. This is followed by stirring at 3-5° C. for one hour. The crystals are filtered off with suction and washed with toluene. The hemisolvate of 2-(3-hydroxyphenoxymethyl)-6-methylbenzoic acid * 0.5 NMP is obtained in a yield of 82%; melting point 112 to 113° C.

2-(3-Hydroxyphenoxymethyl)-6-methylbenzoic Acid (Nonsolvate)

5.0 g (14 mmol) of 2-(3-hydroxyphenoxymethyl)-6-methylbenzoic acid * NMP are heated under reflux in 50 ml of water for two hours. After cooling, the resulting solid is filtered off with suction and washed with water. 2-(3-Hydroxyphenoxymethyl)-6-methylbenzoic acid is obtained in a yield of 86.4%; melting point 154 to 155° C.

EXAMPLE 1.2

2-(3-Hydroxyphenoxymethyl)benzoic Acid

Phthalide (15.0 g, 112 mmol), resorcinol (23.6 g, 214 mmol) and potassium tert-butoxide (47.6 g, 220 mmol) are suspended in 150 ml of N-methylpyrrolidone (NMP) and stirred at 140° C. for 5 h. The reaction mixture is cooled, 400 ml of water are added, and the mixture is acidified to pH=4 at 20° C. with concentrated hydrochloric acid. The solution is extracted once with 200 ml of ethyl acetate and four times with 100 ml of ethyl acetate. The combined ethyl acetate phases are dried over magnesium sulfate and evaporated to dryness. A pale brown oil is obtained and crystallizes at 0° C. The crystals comprise a mixture of 2-(3-hydroxyphenoxymethyl)benzoic acid and the dialkylated resorcinol. This mixture is heated with 10 times the amount of ethyl acetate to dissolve the 2-(3-hydroxyphenoxymethyl)benzoic acid, the dialkylated product remaining as solid. The ethyl acetate phase is evaporated to dryness, whereupon 2-(3-hydroxyphenoxymethyl)benzoic acid remains as pale beige crystals.

$^1$H NMR (400 MHz, DMSO-d6) δ

13.1 (br s, 1H, COOH), 9.4 (br s 1H, OH), 7.92 (q, 1H), 7.64-7.57 (2H), 7.43 (dt 7.06 (m, 1H), 6.41-6.34 (3H), 5.34 (s, 2H, CH$_2$)

b) Correspondingly overalkylated product of the formula (IV)

13.1 (br s 2H, COOH), 7.94 (d, 2H), 7.66-7.58 (4H), 7.45 (d, 2H), 7.21 (t, 1H), 6.62-6.58 (2H), 5.44 (s, 4H, CH$_2$)

EXAMPLE 1.3

2-(3-Hydroxyphenoxymethyl)-6-methyl-benzoic acid and the solvate thereof with N,N-dimethylacetamide 2-(3-Hydroxyphenoxymethyl)-6-methyl-benzoic acid (solvate with N,N-dimethylacetamide in the Ratio 5:2)

The procedure takes place in analogy to Example 1.1, but N,N-dimethylacetamide (DMAA) is employed in place of N-methylpyrrolidone (NMP). The product is purified by recrystallization from toluene. Both the crude product and the recrystallized product have a 2-(3-hydroxyphenoxymethyl)-6-methyl-benzoic acid:DMAA ratio of 5:2. The yield is 60.0%, melting point 112-114° C.

2. PREPARATION OF COMPOUNDS OF THE GENERAL FORMULA(I)

EXAMPLE 2.1

2-{3-[2-(4-Fluorophenyl)oxazol-4-ylmethoxy]phenoxymethyl}-6-methylbenzoic acid a) in N-methylpyrrolidone as solvent 18.6 g of 30% strength solution of sodium methoxide in methanol (104 mmol) are added to 15.9 g (51.6 mmol) of 2-(3-hydroxyphenoxymethyl)-6-methyl-benzoic acid (hemisolvate with N-methylpyrrolidone) in 70 ml of N-methylpyrrolidone while stirring at room temperature. After five minutes, 10.0 g (47.3 mmol) of 4-chloromethyl-2-(4-fluorophenyl)oxazole are added, and the mixture is stirred at room temperature for 23 h and finally heated at 50° C. for one hour. 500 ml of 19% strength sodium chloride solution are added to the reaction solution, and the resulting mixture is extracted twice with 225 ml of ethyl acetate. The combined ethyl acetate phases are extracted three times with 225 ml of water, and the combined aqueous phases are acidified to pH=3 with 2 M hydrochloric acid. The resulting crystals are filtered off with suction and washed with water. The product is purified further by crystallization from isopropanol. 2-{3-[2-(4-Fluorophenyl)oxazol-4-ylmethoxy]phenoxymethyl}-6-methylbenzoic acid is obtained as colorless crystals in a yield of 58.3%, melting point 168-173° C.

$^1$H NMR (400 MHz, DMSO-d6)δ

13.2 (br s, 1H, COOH), 8.29 (s, 1H, oxazole H), 8.04 (m, 2H, fluorophenyl H), 7.39 (m, 2H, fluorophenyl H), 7.35-7.31 (m, 2H), 7.25 (m, 1H), 7.20 (m, 1H), 6.67-6.65 (m, 2H), 6.58 (dd, 1H), 5.11 (s, 2H, CH$_2$), 5.03 (s, 2H, CH$_2$), 2.33 (s, 3H, CH$_3$)

b) in methanol as solvent

The reaction is carried out as described under a). The reaction temperature is 50° C. over the entire period of 24 hours. 2-{3-[2-phenyloxazol-4-ylmethoxy]phenoxymethyl}-6-methylbenzoic acid is obtained as colorless crystals in a yield of 53.0%.

EXAMPLE 2.2

6-Methyl-2-[3-(2-phenyloxazol-4-ylmethoxy)phenoxymethyl]benzoic acid

The procedure takes place in analogy to Example 2.1, but 4-chloromethyl-2-phenyloxazole is employed in place of 4-chloromethyl-2-(4-fluorophenyl)oxazole. 2-{(3-[2-(4-Fluorophenyl)oxazo 4-ylmethoxy]phenoxymethyl}-6-methylbenzoic acid is obtained as colorless crystals in a yield of 45.0%.

$^1$H NMR (400 MHz, DMSO-d6)δ

13.2 (br s, 1H, COOH), 8.29 (s, 1H, oxazole H), 8.02-8.00 (m, 2H), 7.56-7.52 (m, 3H), 7.37-7.19 (4H), 6.69-6.59 (3H), 5.13 (s, 2H, CH$_2$), 5.05 (s, 2H, CH$_2$),

EXAMPLE 2.3

2-(3-Benzyloxyphenoxymethyl)-6-methylbenzoic acid

The procedure takes place in analogy to Example 2.1, but benzyl bromide is employed in place of 4-chloromethyl-2-(4-fluorophenyl)oxazole. 2-(3-Benzyloxyphenoxymethyl)-6-methylbenzoic acid is obtained as colorless crystals in a yield of 47.3%.

$^1$H NMR (400 MHz, DMSO-d6)δ

13.2 (br s, 1H, COOH), 7.45-7.30 (7H), 7.25 (m, 1H), 7.18 (t, 1H), 6.63-6.55 (3H), 5.10(s, 2H, CH$_2$), 5.07 (s, 2H, CH$_2$), 5.34 (s, 3H, CH$_3$)

COMPARATIVE EXAMPLE 2.4

(2-{3-[2-(4-Fluorophenyl)oxazol-4-ylmethoxy]phenoxymethyl-}-6-methylbenzoic acid 1 g (6.8 mmol) of 7-methylphthalide and 2 g (7.0 mmol) of 3-[2-(4-fluorophenyl)oxazol-4 -ylmethoxy]phenol are dissolved in NMP. 3.9 ml of methanolic sodium methoxide (30% strength) are added, the methanol is distilled off, and the mixture is heated to 130° C. No formation of 2-{3-[2-(4-fluorophenyl)oxazol-4-ylmethoxy]phenoxymethyl}-6-methylbenzoic acid is observed. The 3-[2-(4-fluorophenyl)oxazol-4-ylmethoxy]phenol decomposes.

We claim:

1. A process for preparing a compound of formula (I) comprising the steps of:
    a) reacting a compound of formula (II) in the presence of a base B1 with a compound of formula (III) to provide a compound of formula (IV); and

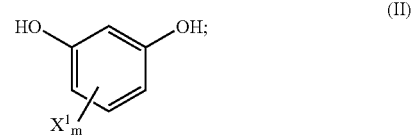

-continued

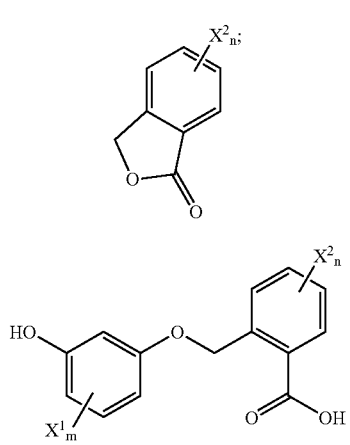
(III)

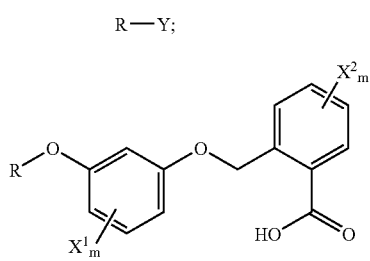
(IV)

b) reacting the compound of formula (IV) in the presence of a base B2 with a compound of formula (V) to provide a compound of formula (I)

R—Y;  (V)

(I)

wherein
R is selected from the group consisting of unsubstituted or at least monosubstituted $C_1$-$C_{10}$-alkyl, heterocyclyl, aryl-($C_1$-$C_{10}$-alkyl)-, heteroaryl-($C_1$-$C_{10}$-alkyl)- and heterocyclyl-($C_1$-$C_{10}$-alkyl)-,
wherein the substituents are selected from the group consisting of halogen, $C_1$-$C_6$-alkyl, —O-aryl, oxo, $C_1$-$C_6$-alkoxy, —C(O)O—($C_1$-$C_6$-alkyl), $C_2$-$C_6$-alkenyl, $C_2$-$C_6$-alkynyl, —C(O)—($C_1$-$C_6$-alkyl), —C(O)$NH_2$, —C(O)NH($C_1$-$C_6$-alkyl), —C(O)N($C_1$-$C_6$-alkyl)$_2$, —S—($C_1$-$C_6$-alkyl), —$SO_2NH_2$, —$SO_2$—($C_1$-$C_6$-alkyl), —$NH_2$, —N($C_1$-$C_6$-alkyl)$_2$, —NH($C_1$-$C_6$-alkyl), —$NO_2$, —CN, trifluoromethyl, trifluoromethoxy, aryl, heterocyclyl and heteroaryl,
wherein said —O-aryl, aryl, heterocyclyl and heteroaryl may in turn be at least monosubstituted by $C_1$-$C_3$-alkyl, $C_1$-$C_3$-alkoxy, halogen or trifluoromethyl;
$X^1$ is halogen, $C_1$-$C_6$-alkyl, $C_1$-$C_6$-alkoxy, trifluoromethyl, aryl, heterocyclyl or heteroaryl,
wherein said aryl, heterocyclyl and heteroaryl may in turn be at least monosubstituted by $C_1$-$C_3$-alkyl, $C_1$-$C_3$-alkoxy, halogen or trifluoromethyl;
$X^2$ is halogen, $C_1$-$C_6$-alkyl, $C_1$-$C_6$-alkoxy, trifluoromethyl, aryl, heterocyclyl or heteroaryl,
wherein said aryl, heterocyclyl and heteroaryl in turn may be at least monosubstituted by $C_1$-$C_3$-alkyl, $C_1$-$C_3$-alkoxy, halogen or trifluoromethyl;

wherein heteroaryl is a 5-, 6-, 7-, 8-, 9-, 10-, 11-, 12-, 13- or 14-membered, aromatic, mono-, bi- or tricyclic heterocycle which contains one or more heteroatoms selected from N, O and S;
wherein aryl is a 6-, 7-, 8-, 9-, 10-, 11-, 12-, 13- or 14-membered, aromatic mono-, bi- or tricyclic system;
wherein heterocyclyl is a 5-, 6-, 7-, 8-, 9-, 10, 11-, 12-, 13- or 14-membered, nonaromatic, mono-, bi- or tricyclic heterocycle which contains one or more heteroatoms selected from N, O and S;
m is 0, 1, 2, 3 or 4;
n is 0, 1, 2, 3 or 4;
Y is a leaving group; and
B1 is selected from the group consisting of an alkali metal alcoholate, alkaline earth metal alcoholate, silazide or alkali metal hydroxide.
B2 is selected from the group consisting of an alkali metal hydroxide, alkaline earth metal hydroxide, alkali metal alcoholate, alkaline earth metal alcoholate, alkali metal hydride, alkaline earth metal hydride, silazide, alkali metal amide or alkaline earth metal amide.

2. The process of claim 1, wherein B1 is selected from the group consisting of sodium methoxide, potassium methoxide and potassium tert-butoxide.

3. The process of claim 1, wherein B2 is selected from the group consisting of sodium methoxide, potassium methoxide, potassium tert-butoxide, potassium hexamethyldisilazide, lithium hexamethyldisilazide, sodium hydride, calcium hydride, sodium hydroxide and potassium hydroxide.

4. The process of claim 1, wherein the solvent used in step a) is selected from the group consisting of N-methyl-1-pyrrolidone and N,N-dimethylacetamide.

5. The process of claim 1, wherein the solvent used in step b) is selected from the group consisting of an alcohol and a carboxamide.

6. The process of claim 1, wherein step a) is carried out at a temperature between 110 and 150° C. and/or step b) is carried out at a temperature in the range of from 20 up to 50° C.

7. The process of claim 1, wherein
the compound of formula (II) in step a) is employed in exactly equimolar amount to the base B1 and in at least equimolar amount to the compound of formula (III) or the base B2 in step b) is employed in exactly twice the molar amount to the compound of formula (IV) and the compound of formula (III) is employed in 1 to 1.25 times the molar amount to the compound of formula (IV).

8. The process of claim 1, wherein step b) is followed by preparation of a compound having at least one carboxyl, (—SH) or (—OH) substituent by elimination of alkyl from a compound of the formula (I) which has at least one (—C(O)O—($C_1$-$C_6$-alkyl)), (—S—($C_1$-$C_6$-alkyl)) or ($C_1$-$C_6$-alkoxy) substituent.

9. The process of claim 1, wherein
R is selected from the group consisting of:
unsubstituted or at least monosubstituted aryl-($C_1$-$C_6$-alkyl)- and heteroaryl-($C_1$-$C_6$-alkyl)-,
wherein the substituents are selected from the group consisting of halogen, $C_1$-$C_4$-alkyl, —O-aryl, oxo, $C_1$-$C_4$-alkoxy, aryl, heterocyclyl and heteroaryl,
wherein said —O-aryl, aryl, heterocyclyl and heteroaryl may in turn be at least monosubstituted by $C_1$-$C_3$-alkyl, $C_1$-$C_3$-alkoxy, halogen or trifluoromethyl;
$X^1$ is halogen, $C_1$-$C_6$-alkyl, $C_1$-$C_6$-alkoxy or trifluoromethoxy;

X² is halogen, $C_1$-$C_6$-alkyl, $C_1$-$C_6$-alkoxy or trifluoromethoxy;
wherein heteroaryl is a 5-, 6-, 7-, 8-, 9-, 10, 11-, 12-, 13- or 14-membered, aromatic, mono-, bi- or tricyclic heterocycle which contains one or more heteroatoms selected from N, O and S;
wherein aryl is a 6-, 7-, 8-, 9-, 10-, 11-, 12-, 13- or 14-membered, aromatic mono-, bi- or tricyclic system;
wherein heterocyclyl is a 5-, 6-, 7-, 8-, 9-, 10-, 11-, 12-, 13- or 14-membered nonaromatic, mono-, bi- or tricyclic heterocycle which contains one or more heteroatoms selected from N, O and S;
m is 0, 1 or 2;
n is 0, 1 or 2; and
Y is a leaving group.

10. The process of claim 9, wherein
R is unsubstituted or at least monosubstituted benzyl or heteroarylmethyl, wherein the substituents are selected from fluorine, chlorine, $C_1$-$C_4$-alkyl, —O-phenyl, $C_1$-$C_4$-alkoxy, phenyl and heteroaryl,
wherein said —O-phenyl phenyl and heteroaryl may in turn be at least monosubstituted by $C_1$-$C_3$-alkyl, $C_1$-$C_3$-alkoxy, chlorine or fluorine;
X¹ is $C_1$-$C_3$-alkyl or bromine;
X² is $C_1$-$C_3$-alkyl, fluorine or chlorine;
wherein heteroaryl is selected from the group consisting of oxazolyl, isoxazolyl, oxadiazolyl, thiazolyl, isothiazolyl, pyridinyl, pyridazinyl, pyrimidinal, pyrazinyl, indolyl, benzimidazolyl, quinolinyl, isoquinolinyl, quinazolinyl or quinoxalinyl;
m is 0 or 1;
n is 0, 1 or 2; and
Y is chlorine, bromine or iodine.

11. A process for preparing the compound of formula (IV) comprising:

reacting a compound of formula (II) in the presence of a base B1 with a compound of formula (III) to provide a compound of formula (IV);

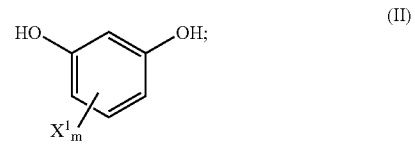

(II)

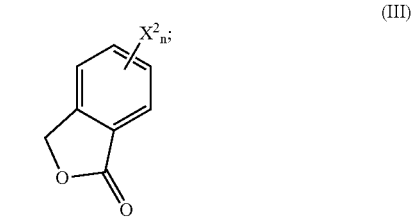

(III)

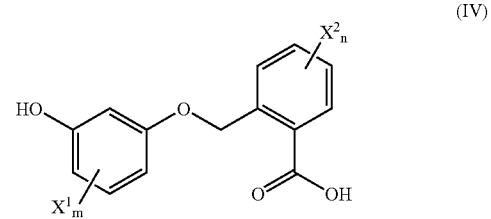

(IV)

Wherein B1 is selected from the group consisting of an alkali metal alcoholate, alkaline earth metal alcoholate, silazide or alkali metal hydroxide.

* * * * *